(12) United States Patent
Murphy et al.

(10) Patent No.: US 10,716,939 B2
(45) Date of Patent: Jul. 21, 2020

(54) METHODS AND SYSTEMS FOR INTERSPERSE PAIN TREATMENT

(71) Applicant: International Rehabilitative Sciences, Inc., Vancouver, WA (US)

(72) Inventors: Randy Alan Murphy, Vancouver, WA (US); William J. Carroll, LaCenter, WA (US); Richard M. Terrell, Vancouver, WA (US)

(73) Assignee: International Rehabilitative Sciences, Inc., Vancouver, WA (US)

( * ) Notice: Subject to any disclaimer, the term of this patent is extended or adjusted under 35 U.S.C. 154(b) by 13 days.

(21) Appl. No.: 15/461,677

(22) Filed: Mar. 17, 2017

(65) Prior Publication Data

US 2018/0193640 A1    Jul. 12, 2018

Related U.S. Application Data

(60) Provisional application No. 62/444,843, filed on Jan. 11, 2017.

(51) Int. Cl.
*A61N 1/36* (2006.01)
*A61N 1/04* (2006.01)

(52) U.S. Cl.
CPC ....... *A61N 1/36021* (2013.01); *A61N 1/0452* (2013.01); *A61N 1/36003* (2013.01)

(58) Field of Classification Search
CPC . A61N 1/36003; A61N 1/36014; A61N 1/323
See application file for complete search history.

(56) References Cited

U.S. PATENT DOCUMENTS

| | | | |
|---|---|---|---|
| 6,393,328 B1 * | 5/2002 | McGraw | A61N 1/326 607/67 |
| 6,560,487 B1 | 5/2003 | McGraw et al. | |
| 2004/0015203 A1 | 1/2004 | McGraw et al. | |
| 2005/0278001 A1 * | 12/2005 | Qin | A61N 1/37247 607/48 |
| 2007/0021802 A1 | 1/2007 | Heruth et al. | |
| 2011/0295339 A1 * | 12/2011 | Carroll | A61N 1/0452 607/49 |

OTHER PUBLICATIONS

Ray C, "Electrical Stimulation: New Methods for Therapy and Rehabilitation", Scand J Rehab Med 10: 65-74, 1978.
Robinson A, Snyder-Mackler L, Clinical Electrophysiology, 2nd Edition. Williams & Wilkins, Baltimore, MD, 1995, p. 53-67.
De Domenico G, New Dimensions in Interferential Therapy A Theoretical & Clinical Guide, Reid Medical Books, Lindfield, Australia, 1987.

(Continued)

*Primary Examiner* — George R Evanisko
(74) *Attorney, Agent, or Firm* — McDonnell Boehnen Hulbert & Berghoff LLP

(57) ABSTRACT

An example method includes sending a muscle stimulation current treatment signal to one or more electrodes. The muscle stimulation current treatment signal alternates between on-off states. The method further includes sending, while the muscle stimulation current treatment signal is off, an interferential current treatment signal to the one or more electrodes.

19 Claims, 10 Drawing Sheets

(56) References Cited

OTHER PUBLICATIONS

Interferential Therapy, Monograph, B.V. Enraf-Nonius, Delft, Holland, Dec. 2005.
The Practice of Minimally Invasive Spinal Technique (Savitz M, Chiu J, Yeung A, eds), AAMISMS Education, LLC, Richmond, VA, 2000, Chapter 43, p. 341-346.
Yeung A, Porter J, "Effect of sequential electrical surface stimulation on medication utilization following Selective Endoscopic Discectomy™ Initial evaluation", J of Minimally Invasive Spinal Technique 2: 26-27, 2002.
Glaser J, Baltz M, Nietert P, and Benson C, "Electrical Muscle Stimulation as an Adjunct to Exercise Therapy in the Treatment of Nonacute Low Back Pain: A Randomized Trial", Journal of Pain 2: 295-300, 2001.
International Search Report and Written Opinion prepared by the U.S. Patent Office in International application No. PCT/US18/12952 dated Apr. 5, 2018.

\* cited by examiner

METHODS AND SYSTEMS FOR INTERSPERSE PAIN TREATMENT

CROSS-REFERENCE TO RELATED PATENT APPLICATION

The present disclosure claims priority to U.S. patent application No. 62/444,843, filed on Jan. 11, 2017, the entire contents of which are herein incorporated by reference.

BACKGROUND

Unless otherwise indicated herein, the materials described in this section are not prior art to the claims in this application and are not admitted to be prior art by inclusion in this section.

Numerous electrical devices are commonly used in medicine today, most of them dating back some forty years or more. While these devices are still being used, recent technological innovations and improved protocols have continued to advance their utility. Physicians today use electrical devices for many purposes. A pacemaker senses the heart's electrical activity and stimulates it to normalize the heart rate. An Electroencephalograph (EEG) measures the electrical output of brain activity. The EMG measures motor and sensory nerve activity. A Bone Growth Device electrically propagates long bone growth and augments spinal fusion surgery. A Transcutaneous Electrical Nerve Stimulator (TENS) is commonly used in physical therapy for temporary pain control. A Neuromuscular Electrical Stimulator (MMES) contracts muscle to normalize its function.

Spinal Cord Stimulation devices are used in cases of chronic, debilitating pain. Current methods of pain treatment may involve multiple therapy sessions. One therapy session can include treating a patient with interferential ("IF") therapy. IF therapy sessions can be used when a patient has chronic pain. Another therapy session can include treating the patient with muscle stimulation ("MS") therapy. MS therapy sessions can be used when a patient has acute pain and/or dis-use atrophy. Administering these multiple therapy sessions are often time consuming for the patient, and may not provide adequate treatment. Such administration is also often uncomfortable for patients, because a physician may have to change the position of electrodes between therapy sessions.

SUMMARY

In one example, a method of pain treatment is described that comprises sending, by an electro-medical device, a muscle stimulation current treatment signal to one or more electrodes. The muscle stimulation current treatment signal alternates between on-off states. The method also comprises sending, by the electro-medical device while the muscle stimulation current treatment signal is in an off state, an interferential current treatment signal to the one or more electrodes.

In another example, an electro-medical device is described that comprises one or more drive circuits to output treatment signals on one or more channels, and a processor coupled to the one or more drive circuits to send a muscle stimulation current treatment signal having an on-off duty cycle through the one or more drive circuits to the one or more channels, and to send an interferential current treatment signal through the one or more drive circuits to the one or more channels while the muscle stimulation current treatment signal is in an off state of the duty cycle.

In another example, a non-transitory computer readable medium is described having stored therein instructions that, when executed by a processor of an electro-medical device, cause the electro-medical device to perform functions. The functions comprise sending a muscle stimulation current treatment signal to one or more electrodes. The muscle stimulation current treatment signal alternates between on-off states. The functions also comprise sending, while the muscle stimulation current treatment signal is in an off state, an interferential current treatment signal to the one or more electrodes.

These as well as other embodiments, aspects, advantages, and alternatives will become apparent to those of ordinary skill in the art by reading the following detailed description, with reference where appropriate to the accompanying drawings. Further, this summary and other descriptions and figures provided herein are intended to illustrate embodiments by way of example only and, as such, that numerous variations are possible. For instance, structural elements and process steps can be rearranged, combined, distributed, eliminated, or otherwise changed, while remaining within the scope of the embodiments as claimed.

DETAILED DESCRIPTION

Figure 1:
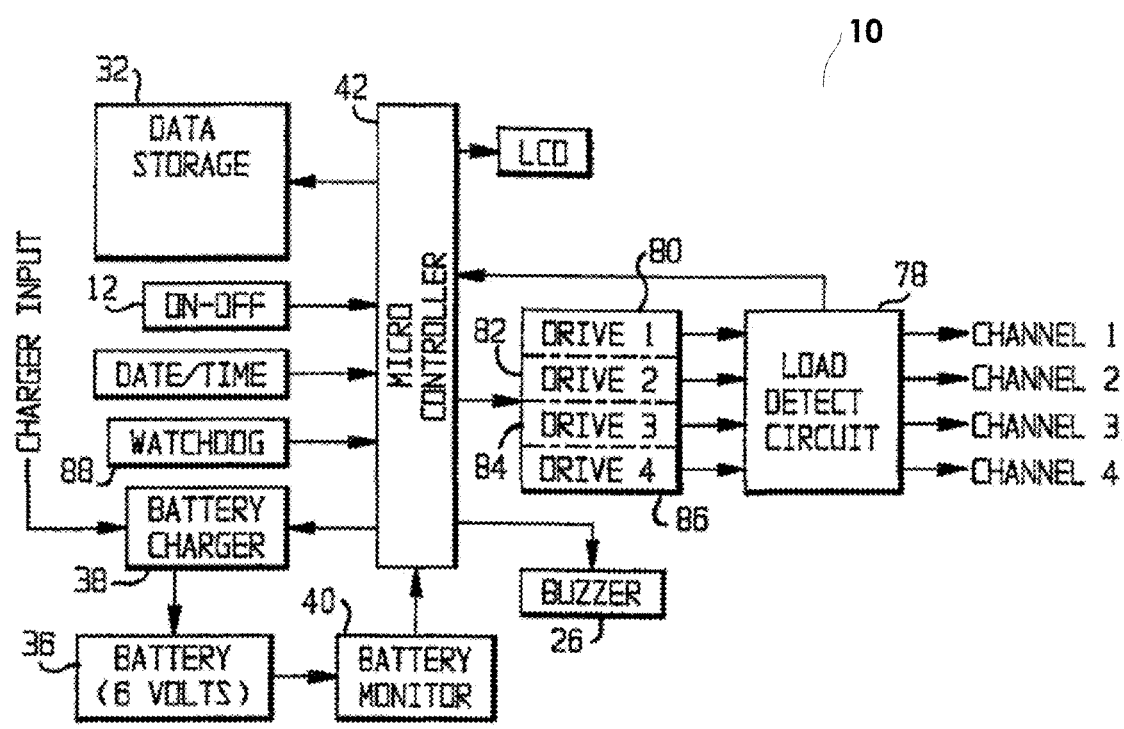
FIG. 1 is a schematic block diagram of a multi-functional portable electro-medical device, according to an example embodiment.

Example methods, devices, and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Other embodiments can be utilized, and other changes can be made, without departing from the scope of the subject matter presented herein.

Thus, the example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are contemplated herein.

Further, unless context suggests otherwise, the features illustrated in each of the figures may be used in combination with one another. Thus, the figures should be generally viewed as component aspects of one or more overall embodiments, with the understanding that not all illustrated features are necessary for each embodiment.

Additionally, any enumeration of elements, blocks, or steps in this specification or the claims is for purposes of clarity. Thus, such enumeration should not be interpreted to require or imply that these elements, blocks, or steps adhere to a particular arrangement or are carried out in a particular order.

Example methods described herein include methods for treating chronic, acute pain, and dis-use atrophy in patients. One therapy that has proven useful for rehabilitation has been Sequential Electrical Surface Stimulation, which delivers interferential stimulation to relieve pain so the patient can then receive neuromuscular stimulation for underlying conditions. Another example stimulation therapy is Intersperse Stimulation, which is combination of electrical stimulation waveforms and has demonstrated a preference when compared to a traditional sequential NMES.

One example method for treating pain described herein includes sending, by an electro-medical device, a muscle stimulation current treatment signal to one or more electrodes positioned on a patient. The muscle stimulation current treatment signal alternates between on-off states. The method also includes sending, while the muscle stimulation current treatment signal is off, an interferential current treatment signal to the one or more electrodes positioned on the patient. Using this method enables more efficient pain treatment, as well as, improved muscle stimulation treatment due to the interferential current treatment signal aiding in the removal of build-up of lactic acid in the muscle and increasing blood flow.

Example methods of treatment, referred to as intersperse stimulation, takes advantage of the off time of the muscle stimulation duty cycle. Usually, the off time is a period of no stimulation or electrical silence. In example methods, the off time of the duty cycle is filled with premodulated Interferential stimulation. This reduces a duration of treatment for a patient, and this combination of waveforms produces a more profound analgesia.

Example benefits of intersperse stimulation are that it saves treatment time and that a more complete analgesia can be achieved because interferential stimulation is sent through the electrodes during the normally quiescent "off time" of the NMES duty cycle.

Many electro-medical devices may be used for this treatment, and one example is described below.

FIG. 1 is a schematic block diagram of a multifunctional portable electro-medical device 10, according to an example embodiment. The exemplary electro-medical device 10 can be powered by a rechargeable 7.2 volt nickel cadmium or nickel Hydride battery system 36, which is recharged, by a battery charger 38, that may be powered by standard 110 volt household electric current. As a safety feature, the electro-medical device 10 is designed to be inoperative while the battery system 36 is being charged. A battery monitor circuit 40 is connected between the battery system 36 and a processor 42 so that the processor 42 can provide an indication to the user by means of a LCD touch screen 14 under certain adverse battery conditions as will be described later herein. The processor 42 serves to control and monitor all of the functions of the electro-medical device 10.

Figure 2:
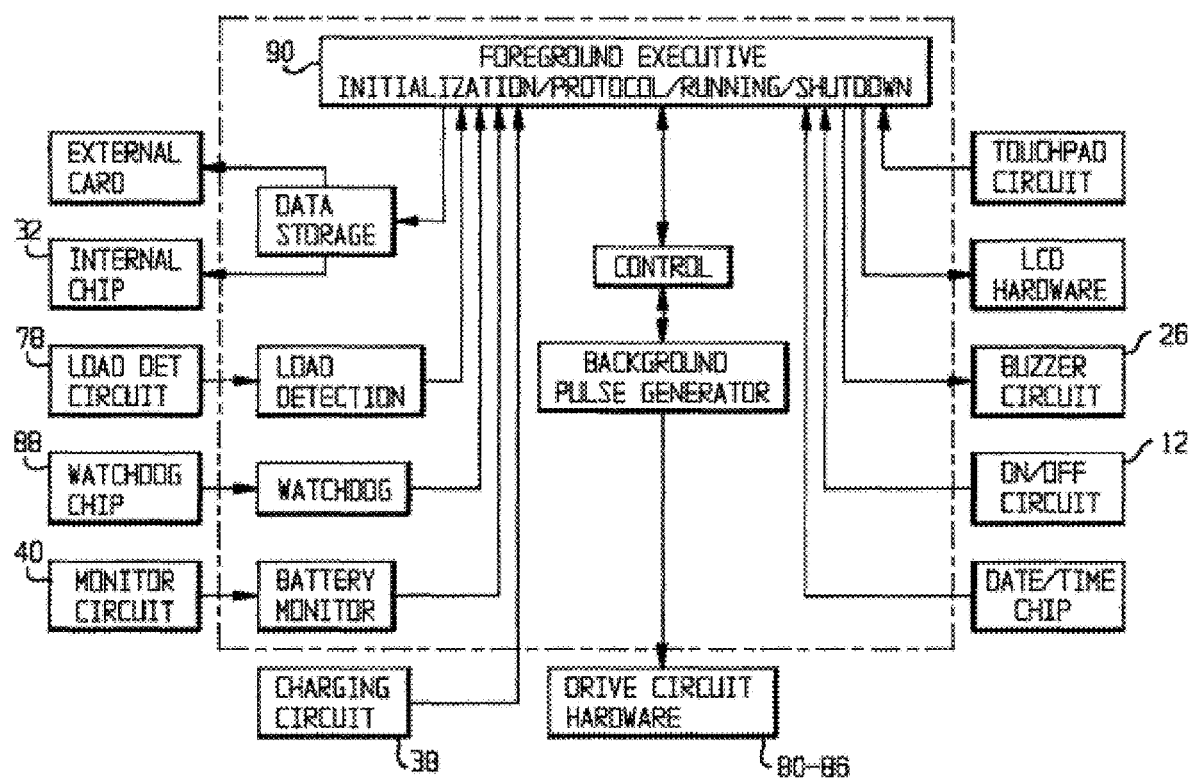
FIG. 2 is a schematic block diagram of an architecture for a multi-functional portable electro-medical device, according to an example embodiment.

As shown in FIG. 2 described more fully below, functions of the device 10 may be implemented with the processor 42. However, functions of the device 10 can also be implemented using a programmed microprocessor and any necessary peripheral integrated circuit elements, an ASIC or other integrated circuit, a hardwired electronic or logic circuit such as a discrete element circuit, a programmable logic device such as a PLD, PLA, FPGA or PAL, or the like.

An example embodiment of the portable electro-medical device 10 provides four electrically isolated channels 1-4 that may be capable of independently treating four separate muscle groups. Each of the four channels may have an independent drive system 80-86. Each drive system may include independent output power stages and transformers that ensures channel separation. The processor 42 may be programmed to control the drive circuits 80-86 to provide any type of electro-medical treatment. A buzzer 26 may provide audible reinforcement to the user of keystroke actions using the LCD touch screen 14. Although this detailed description refers to a device that includes only four channels, it is understood by those of ordinary skill in the art that a device may include any number of channels.

In operation of an exemplary embodiment, a patient may first power up the electro-medical device 10 using an on/off switch 12. If the patient does not desire to change the settings entered into an internal memory 32 of the electro-medical device 10, then the electro-medical device 10 may be powered up in the previously set mode of operation. The default setting is the normal mode. In that normal mode, all four channels of the electro-medical device act synchronously, providing the stimulation pulse trains at the same time, although the intensities of each channel are independently controlled. This mode of operation allows the patient to independently treat up to four separate muscle groups simultaneously.

If the patient desires, an additional level of control for special situations has been provided, which is termed the alternate mode of operation. In the alternate mode of operation, channels 1 and 2 are operated asynchronously with channels 3 and 4. Thus, when channels 1 and 2 are stimulating the muscles, channels 3 and 4 are off, and when channels 1 and 2 are off, channels 3 and 4 are stimulating the muscles. The set on and off times are the same for all four channels in the normal mode.

In an inferential mode of an example embodiment, the continuous mode of operation has two four pad interferential channels. In the continuous mode, the interference frequency is adjustable from 0 to 200 beats per second. In addition, an amplitude modulation feature is selectable which will reduce the amplitude to 50 percent of the user selected value over a five second period and then return to the user selected value, then repeat the process. In the variable mode of operation, the interference frequency is varied during operation. Three variable modes are provided: a low range of 1-10 beats per second, a high range of 80-150 beats per second and a wide range of 1-150 beats per second. The frequency in all three ranges varies over a ten second period. In both the continuous and variable modes of operation, a pre-mixed two pad mode can be selected. In the two pad mode of operation the interference signals are pre-mixed and then outputted across one cable per channel.

In the pulsed muscle stimulation mode, the electro-medical device 10 may generate an alternating biphasic asymmetric balanced pulse pattern with a cycle frequency of 71

Hz, a 100 volt peak and a 60 milliamp peak, for example. The primary pulse can have a maximum width of 415 microseconds, for example, followed by a transformer-coupled exponential decay back to the zero base line. The biphasic pulses alternate direction, resulting in a pulse repetition rate of 142 pulses per second, for example. As previously described, the stimulus intensity is regulated by the patient by pressing the buttons 50. The voltage level is kept constant. The resulting increase or decrease in stimulus intensity is a result of the increasing or decreasing charge per pulse, which is approximately equal to the pulse width times the pulse height. The muscle stimulation pulses are ramped on and off to increase the pulse width to the desired setting and to provide a smooth transition for each muscle contraction.

In the pulsed muscle stimulation mode, a train of repeating pulses is created during the contract cycle. The series of pulses continues until the end of the contract cycle. The relax cycle does not have any pulses. The contract and relax cycles are repeated until the end of the treatment.

In the interferential mode, the electro-medical device 10 may generate a symmetric biphasic sine wave pattern having a carrier frequency of less than 20 KHz, and preferably between about 5-20 KHz, for example. For a carrier frequency of 5000 Hz, an interference frequency is provided of an adjustable 5000-5200 Hz, for example. The output current is 100 milliamps peak to peak on a 500 ohm load, for example. The carrier and interferential signals are true sine wave symmetric biphasic outputs with zero net charge. The two sine waves are mixed in the patient's body when in four-pad mode. In two-pad mode the sine waves are pre-mixed in the electro-medical device and only one pre-mixed output is generated. The sine wave generation continues until the end of the treatment.

By the term "about" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

An example embodiment of the electro-medical device 10 can be preset to modulate the sine wave outputs. Two types of modulation are provided. The first type of modulation is frequency modulation. Three ranges of modulation can be selected: 1-10 beats per second, 80-150 beats per second, and 1-150 beats per second, for example.

The second type of modulation, amplitude modulation, can be selected when the interference frequency is held constant. This type of modulation varies the amplitude of one output from its preset value downward to 50 percent of its preset value over a five second period. The amplitude then returns to its preset value over another five second period. This same amplitude modulation is then repeated for the other output and the process is continuously repeated. Further to an exemplary embodiment, each channel is connected to two pads and the channels are configured so that the modulation on a first channel is opposite to the modulation on the second channel. That is, as the amplitude on the first channel is decreased downward, the amplitude on the second channel returns to the preset value. Amplitude modulation can be performed in both the normal mode and the alternate mode of operation.

The load detect circuit 78 shown in FIG. 1 may include an output voltage signal which is measured across a known load resistance. That signal is amplified and fed back into the analog-to-digital conversion system contained within the processor 42, which allows a precise measurement of the actual load experienced across the output of the transformer contained in each of the four drive circuits 80-86. That measurement allows the processor 42 to detect both open circuits (that is, no load conditions) and short circuit conditions, which allows the processor 42 to shut down the control signals going to the pulse generation circuits which form part of the drive circuits 80-86. Thus, under open or short circuit conditions, the load detection circuit 78 operates to shut down the generation of pulses by the electro-medical device 10.

A watchdog system 88 is also provided to the exemplary embodiment to monitor the processor 42 to ensure that the processor 42 is operating and issuing instructions. The watchdog system 88 operates using a counter. If the counter reaches a certain predetermined value, then it operates to shut down the processor 42 and thus the electro-medical device 10. During normal operation, the processor 42 prevents such a shut down from occurring by always resetting the counter of the watchdog system 88 back to zero well before the maximum counter value is reached. In that manner, if the processor 42 becomes non-operational for any reason, the counter of the watchdog system 88 would reach the maximum predetermined value and, thus, shut down the electro-medical device 10.

FIG. 2 shows a schematic block diagram of an architecture for a multi-functional portable electro-medical device, according to an example embodiment. FIG. 2 illustrates the interfaces between the hardware modules and the control routine modules. The primary module is the foreground executive module 90. The foreground executive module 90 provides executive control of the device from startup to shut down. The foreground executive module 90 is programmed as a state machine with the control routine controlling the operational state of the device based upon inputs received from the device hardware. Functions shown in FIG. 2 may be performed by the processor 42. For example, functions of the foreground executive module 90 may be implemented by the processor 42 executing instructions stored in memory.

Figure 3A:
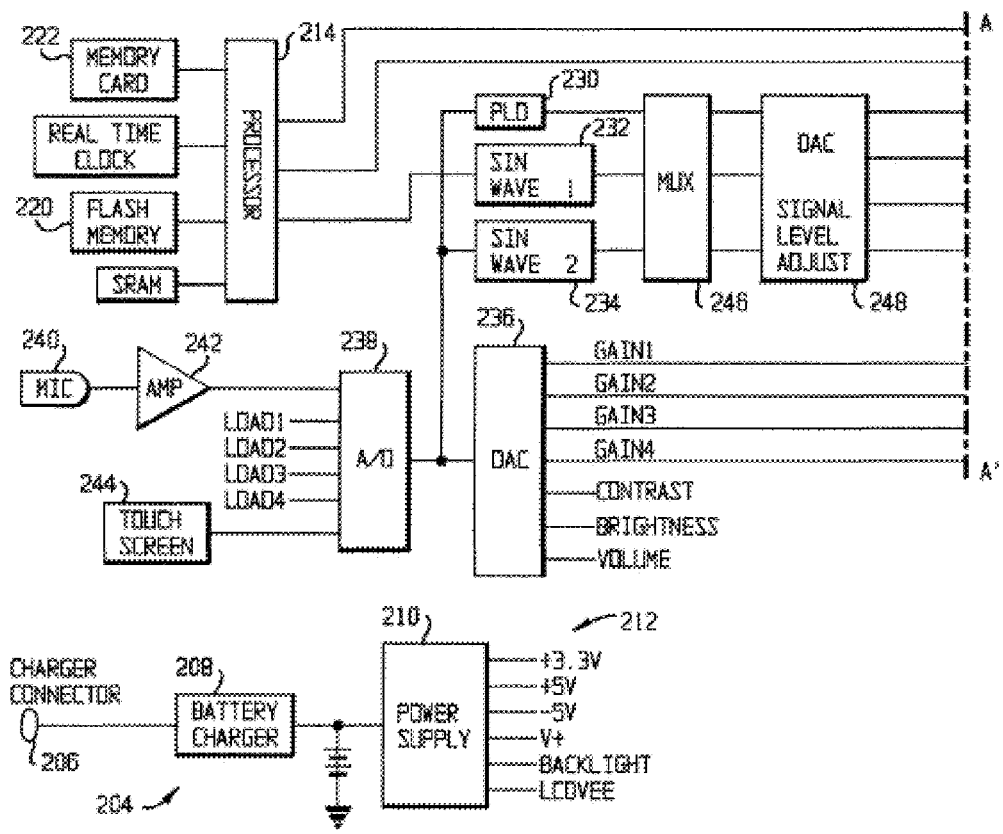
FIGS. 3A and 3B show a schematic diagram of a circuit of a multi-functional portable electro-medical device, according to an example embodiment.
Figure 3B:
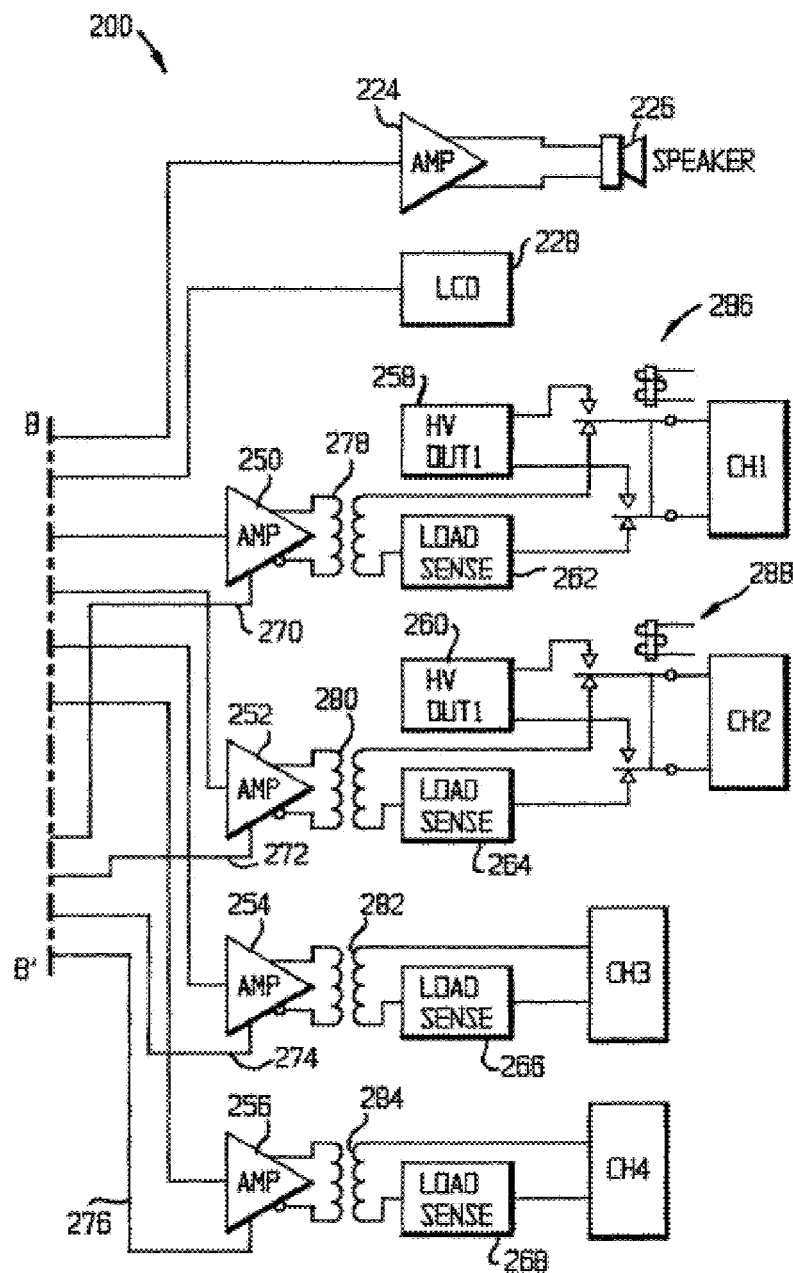

FIGS. 3A and 3B show a schematic diagram of a circuit of a multi-functional portable electro-medical device, according to an example embodiment. The circuit 200 includes a power circuit 204 that has a charger connector 206 in communication with a battery charger 208 in communication with a power supply 210. The power circuit 204 provides a number of outputs 212 that provide power to other portions of the electro-medical device.

The circuit 200 also includes a processor 214 in communication with static RAM 216, flash memory 218, a realtime clock 220, and a memory card 222. The processor 214 is in communication with an amplifier 242 that controls a liquid crystal display 228, a programmable logic device 230, sine wave generators 232 and 234, a digital to analog converter 236 and an analog to digital converter 238. The processor 214 is also in communication with an amplifier 224 that controls a speaker 226. An A to D converter 238 is in communication with a microphone 240 through the amplifier 242 and a touch screen 244. The digital to analog converter provides an output gain 270, 272, 274, 276 to four channels. The processor 214 controls the digital to analog converter 236 to output a predetermined maximum voltage on those outputs. The outputs 270, 272, 274 and 276 provide the input for the amplifiers 250, 252, 254 and 256, respectively.

The processor 214 also communicates with a programmable logic device 230 and sine wave generators 232 and 234 which are multiplexed by a multiplexer 246 to a digital to analog converter 248. The digital to analog converter 248 adjusts the signal level of the amplifiers 250, 252, 254 and 256. The amplifiers 250, 252, 254 and 256 communicate through transformers 278, 280, 282 and 284, respectively. The output of the transformers 282 and 284 are provided directly to the output of channels three and four, respectively. However, the outputs of transformers 278 and 280 are switched through switches 286 and 288 to output channels one and two, respectively. The switches 286 and 288 are solenoids which activate dual bar switches to select the outputs from the transformers 278 and 280 from the high voltage outputs 258 and 260. The circuit 200 also includes load sensing devices 262, 264, 266 and 268 which sense the load of corresponding channels one through four, respectively.

Within examples, the electro-medical device 10 may be operated to implement a two-segment method of combination pain treatment. The first segment may involve the processor 42 sending an interferential current treatment signal through drive circuits 80-86 to channels 1-4 for a pre-defined period of time. The second segment may involve the processor 42 sending a muscle stimulation current treatment signal through drive circuits 80-86 to channels 1-4 on an on-off duty cycle. The second segment may further involve sending another interferential current treatment signal while the muscle stimulation current treatment signal is off.

This method of combination pain treatment may be referred to as "intersperse" pain treatment. Specifically, the electro-medical device 10 may "intersperse" interferential stimulation treatment signals with muscle stimulation signals. This method of interspersing may provide both time and health benefits. For example, a traditional combination pain treatment may involve first treating a patient with interferential therapy, followed by muscle stimulation therapy. Some patients may not be able to spend the time necessary for this type of combination treatment, resulting in longer lasting pain. Examples described below may allow a patient to reduce therapy time in half by combining interferential and muscle stimulation in one therapy treatment.

Intersperse pain treatment may also have health advantages. Muscle stimulation therapy can be harsh on a patient's muscles. The process of muscle stimulation may build up large amounts of lactic acid in the patient's muscles, causing discomfort during the procedure and soreness after the procedure. Interspersing interferential stimulation treatment signals with muscle stimulation treatment signals may allow a patient to recover more quickly in between muscle stimulation contractions. For example, a patient may be receiving a standard muscle stimulation treatment. After each contraction due to the muscle stimulation, lactic acid builds up in the patient's muscle. Some of the lactic acid may flush out in between contractions, but some may still remain. After a period of time, the lactic acid may not subside as quickly as desired. At this point, the patient may experience diminishing returns on the remainder of the muscle stimulation treatment and leave the treatment with sore muscles.

Intersperse pain treatment may be able to lower or eliminate a patient's diminishing returns during treatment. For example, a patient may receive muscle stimulation therapy on an on-off duty cycle of five seconds. While the muscle stimulation therapy is "on," the patient's muscle will contract every five seconds. During the "off" time, interferential stimulation therapy may be applied. Interferential therapy may flush out the lactic acid in the patient's muscle during this "off" time by increasing blood flow. This may remove apparent soreness in the patient's muscle, resulting in a more effective therapy session. Other uses and benefits of intersperse pain treatment may be possible.

Blood flow or blood flow changes may be detected within patients using a variety of devices to determine increases in blood flow during the interferential therapy. An example device may use a form of Doppler ultrasound, in which ultrasound signals are sent into the body and sensors detect the Doppler effect that results as the sound is bounced back from blood moving closer to the sensor and then as it moves farther away again. The device may be positioned on the patient at various locations. Another example device may use photoacoustic imaging in which blood beneath the skin is heated slightly causing a temporary pressure wave that can be detected by sensors. Furthermore, skin sensors and other infrared sensors for fingertip use can be used to detect blood flow, or changes in blood flow, for example.

Turning now to the first segment, the electro-medical device 10 initially is operated to send a continuous interferential stimulation treatment signal to channels 1-4 through drive circuits 80-86.

Figure 4A:
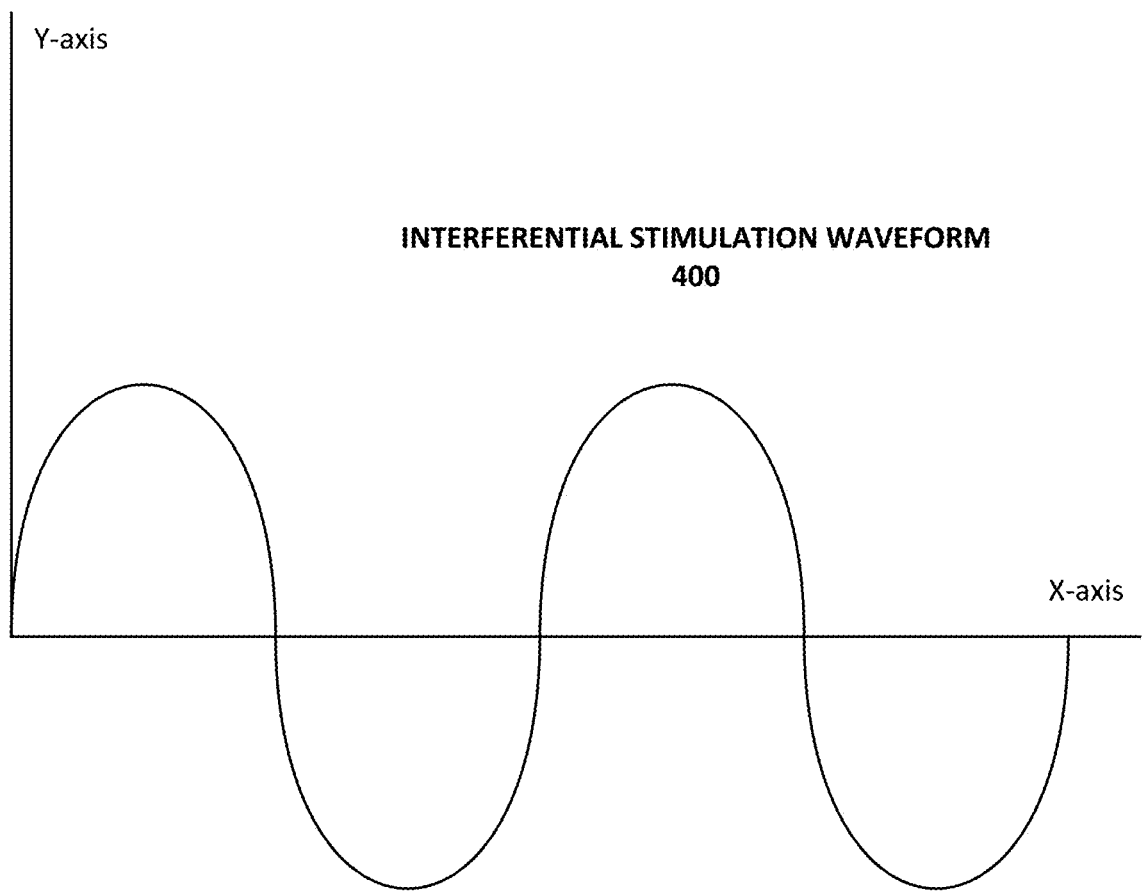
FIG. 4A shows an interferential stimulation waveform, according to an example embodiment.

FIG. 4A shows an interferential stimulation waveform 400, according to an example embodiment. Interferential stimulation waveform 400 may be used to relieve chronic pain by penetrating deep into muscle tissue. Interferential stimulation waveform 400 may be a pre-modulated interferential waveform, in contrast to a true interferential waveform. A true interferential waveform may use two separate circuits outputting two different frequencies in order to create a beat frequency. A pre-modulated interferential waveform uses a processor to increase or decrease the amplitude of the waveform to simulate a true interferential signal.

For example, the processor in electro-medical device 10 may output a sine wave with an amplitude of 5 mA. This results in a peak-to-peak output of 10 mA. The process may use digital signal processing to modify the sine wave to mimic a 100 Hz beat frequency by altering the period of the sine wave to 100 Hz. An example benefit of using a pre-modulated interferential waveform is that the waveform can be implemented on a single circuit with only two electrodes. True interferential waveforms require more than one circuit with more than one electrode.

Figure 4B:
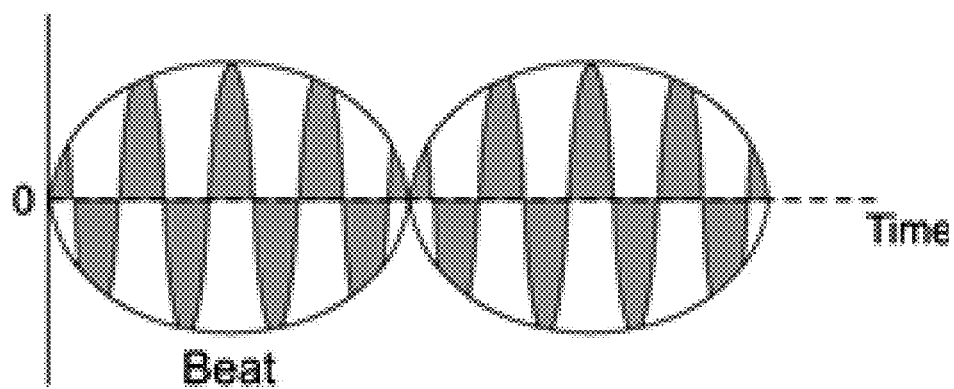
FIG. 4B illustrates another example premodulated interferential waveform, according to an example embodiment.

FIG. 4B illustrates another example premodulated interferential waveform that has a sinewave output with a frequency of approximately 5000 Hz. The amplitude of this output is modulated to simulate a beat frequency that can vary between 10-150 Hz. An advantage of premodulated interferential current is that it can be generated within a single circuit or two electrodes. This removes the necessity of switching electrode configuration during combination treatments, resulting in increased compliance.

The interferential stimulation waveform 400 may be in the form of a sine wave, square wave, or triangle wave. The use of other waveforms is possible. The electro-medical device 10 may output the interferential stimulation waveform 400 during the first segment.

During the first segment, the electro-medical device 10 may output the interferential stimulation waveform 400 from about zero to about fifteen minutes (e.g., within possible tolerances of 10 seconds to 1 minute). The electro-medical device 10 may output the interferential stimulation waveform 400 for a default duration of five minutes; however, the duration can be set by the patient to be shorter or longer.

A patient may control the electro-medical device 10 to set a desired threshold output for the interferential stimulation waveform 400. For example, a patient may slowly increase the amplitude/power output on the electro-medical device to reach a comfortable output. A comfortable output may be an output that makes the patient feel better, but is tolerable. After a patient has set the threshold output, the electro-medical device 10 may store the value of the threshold output for use in the second segment. Thus, a first mode of the treatment is the premodulated Interferential (IF) mode where a comfortable level of IF is set for the overall treatment.

The second segment of the combination pain treatment method may involve alternating between a muscle stimulation signal and an interferential stimulation signal. For example, the electro-medical device 10 may send a muscle stimulation signal with an on-off cycle. While the muscle stimulation signal is off, the electro-medical device 10 may send an interferential stimulation signal. The interferential stimulation signal may be in the form of interferential stimulation waveform 400 discussed in the previous section.

Before the electro-medical device 10 begins the second segment, a patient may determine a desired muscle stimulation amplitude/power. In order to accomplish this, the patient may place one or more electrodes on his or her body, in the area that will receive the treatment. The patient may then increase the amplitude/power until the patient feels a muscle contraction. The amplitude/power the patient reaches during this process may be the amplitude/power applied during the muscle stimulation phase of the second segment.

Figure 5A:
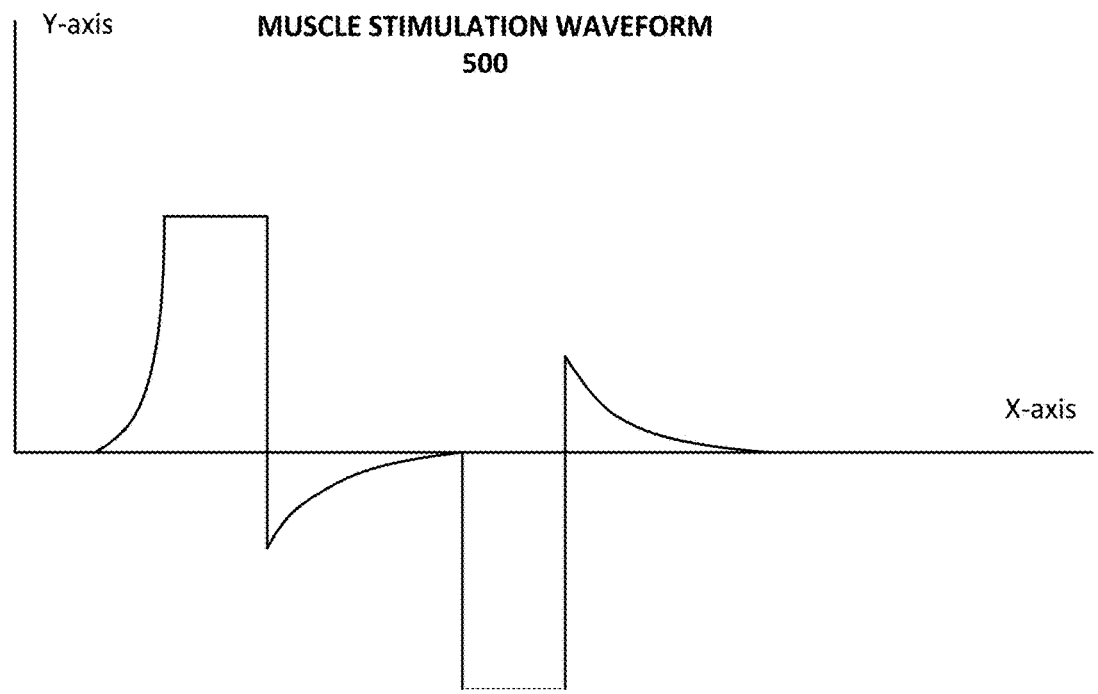
FIG. 5A shows a muscle stimulation waveform, according to an example embodiment.

FIG. 5A shows a muscle stimulation waveform 500, according to an example embodiment. Muscle stimulation waveform 500 may be used to treat acute pain and dis-use atrophy. Muscle stimulation waveform 500 may be used to stimulate longitudinally along a muscle.

Pre-modulation, as described above, involves using a digital signal processor to take an internal frequency and shape the waveform to lower the period of the waveform. The frequency of muscle stimulation waveform 500 may be 30 Hz to 150 Hz, for example, and the period of the waveform may be around 100 times per second. The muscle stimulation waveform 500 may be in the form of a bi-phasic square wave. The electro-medical device 10 may output the muscle stimulation waveform 500 during the on cycle of the muscle stimulation duty cycle.

The muscle stimulation may include Neuromuscular Electrical Stimulation (LAMES). Beneficial effects of muscle stimulation include a reduction of disuse atrophy and an increase in circulation, which can flush out metabolites such as lactic acid that may have been left in the system due to inactivity. This flushing of the system decreases spasticity and normalizes muscle function. The stronger and more complete the contraction, the better the flushing action.

Figure 5B:
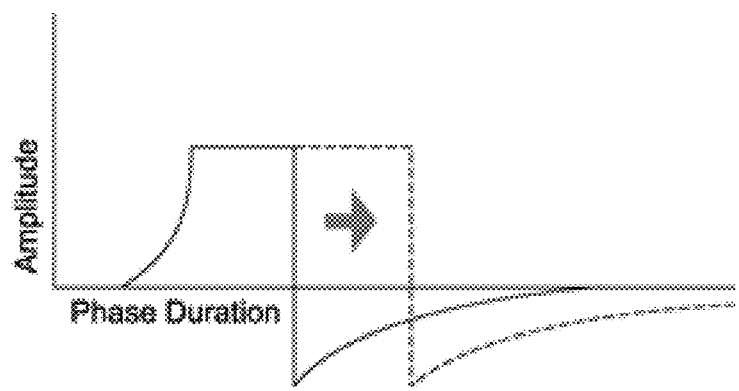
FIG. 5B shows another muscle stimulation waveform, according to an example embodiment.

FIG. 5B shows another muscle stimulation waveform, according to an example embodiment. In FIG. 5B, a phase-duration ramp is shown to increase the intensity of stimulation rather than increasing the amplitude.

Figure 5C:
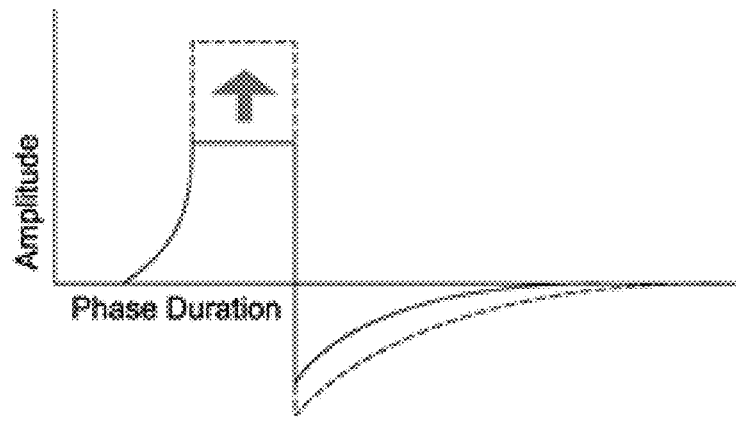
FIG. 5C shows another muscle stimulation waveform, according to an example embodiment.

FIG. 5C shows another muscle stimulation waveform, according to an example embodiment. In FIG. 5C, an amplitude ramp is shown to increase the intensity of stimulation. The phase-duration ramp of FIG. 5B may provide a more comfortable and complete contraction of the muscle than using an amplitude ramp for increasing intensity, as shown in FIG. 5C.

Figure 6:
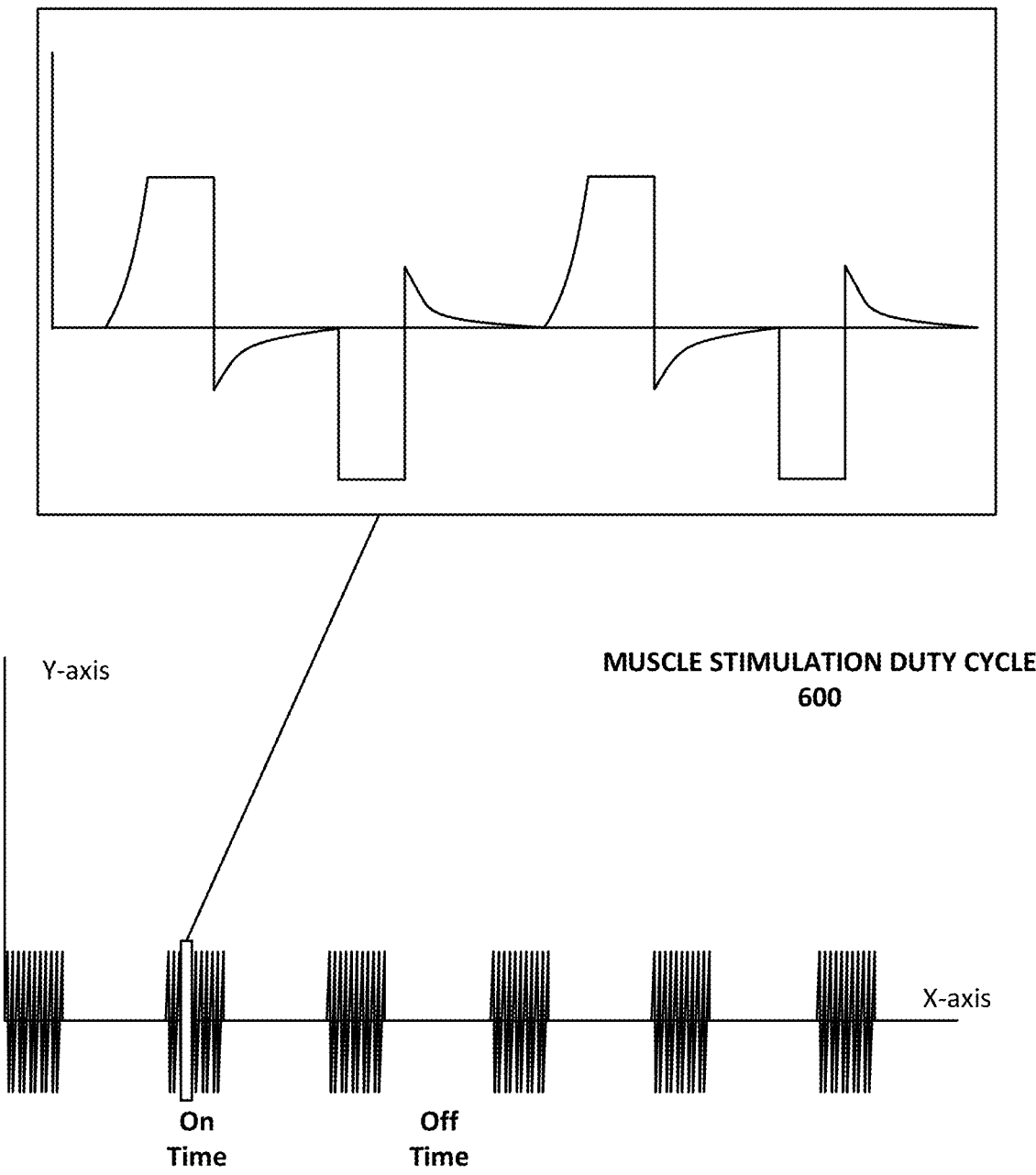
FIG. 6 shows a muscle stimulation duty cycle, according to an example embodiment.

FIG. 6 shows a muscle stimulation duty cycle 600 without interspersing an interferential signal, according to an example embodiment. Muscle stimulation duty cycle 600 may include an "on" state and an "off" state. The "on" and "off" states may vary in length from three seconds to fifteen seconds (or about three second to about fifteen second, plus/minus a few seconds). During the "on" state, muscle stimulation duty cycle 600 may include a series of muscle stimulation waveform 500. For example, assume the muscle stimulation duty cycle 600 has an "on" state of five seconds and an "off" state of five second. During the "on" state, the electro-medical device 10 may output the bi-phasic square wave of muscle stimulation waveform 500 repeatedly. During the "off" state, the electro-medical device may not output a signal. A duration of the "on" and "off" states may vary as well, and may be longer or shorter depending on an application or patient preference.

Figure 7:
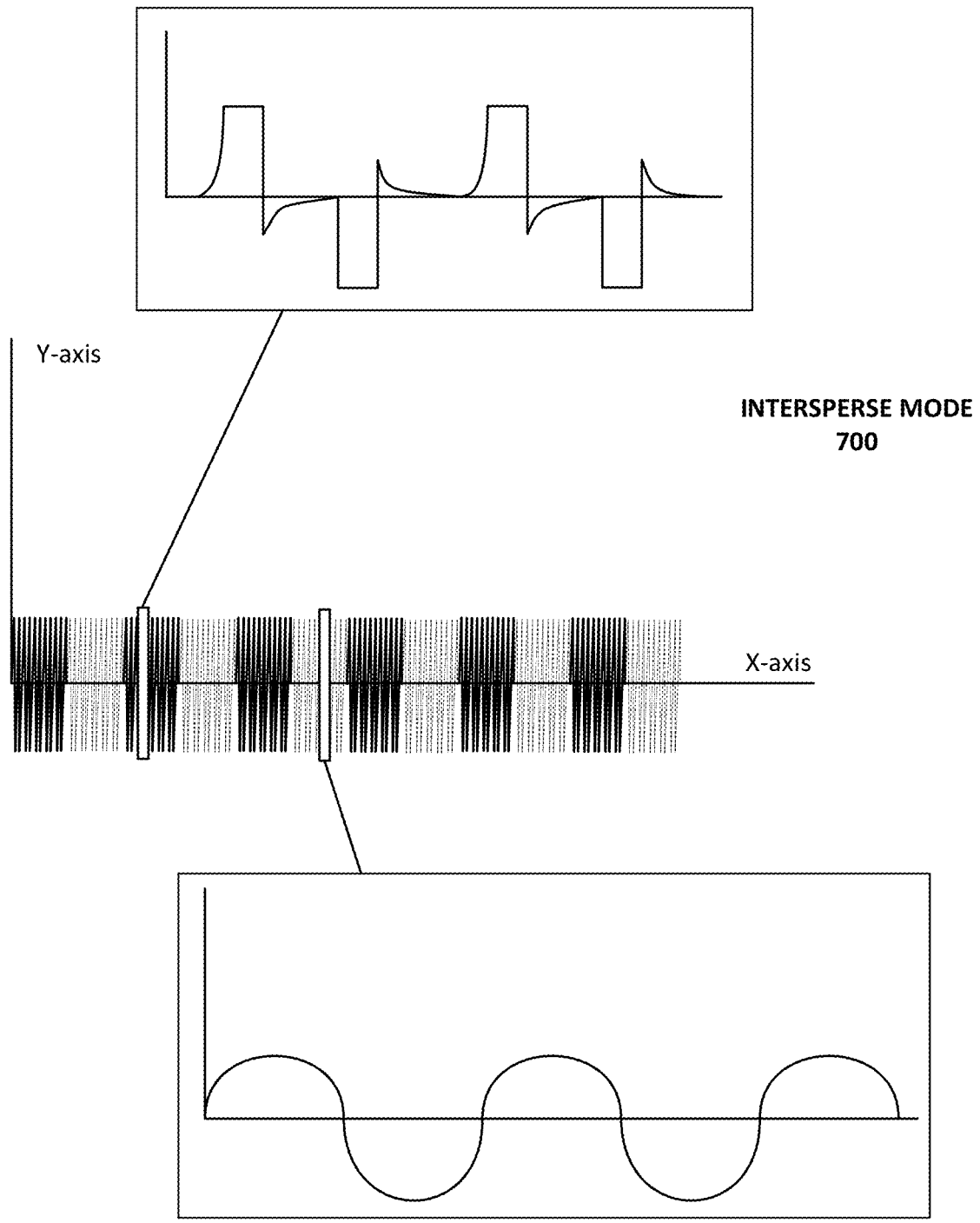
FIG. 7 shows an intersperse operating mode, according to an example embodiment.

FIG. 7 shows an output of intersperse ("IS") mode 700, according to an example embodiment. Intersperse mode 700 may involve electro-medical device 10 alternating the output of muscle stimulation waveform 500 and interferential stimulation waveform 400. During intersperse mode 700, the electro-medical device 10 may begin by sending muscle stimulation waveform 500 for a pre-defined duration as part of a muscle stimulation duty cycle with "on" and "off" states as described above. This pre-defined on-off state duration may vary from three seconds to fifteen seconds (e.g., each state of on and off can be about 3-15 seconds in duration). After the electro-medical device 10 outputs the muscle stimulation waveform 500 for the pre-defined duration, the electro-medical device 10 may enter the "off" state of the muscle stimulation duty cycle.

When the electro-medical device 10 enters the "off" state of the muscle-stimulation duty cycle, it may begin sending the interferential waveform 400. The amount of time electro-medical device 10 sends the interferential waveform 400 may be equal to the duration of the muscle stimulation duty cycle's "on" state. For example, if the muscle stimulation duty cycle has an on-off state duration of five seconds, then the electro-medical device 10 may output the interferential waveform 400 for five seconds. This may be advantageous when the duty cycle duration is short, because the patient may not need an extended period of time to recover from the muscle stimulation "on" cycle.

However, the duration during which the electro-medical device 10 sends the interferential waveform 400 may be longer than the duration of the muscle stimulation duty cycle's "on" state. For example, if the muscle stimulation duty cycle has an on-off state duration of ten seconds, then the electro-medical device 10 may output the interferential waveform 400 for longer than ten seconds. In this case, the electro-medical device 10 may output the muscle stimulation waveform 500 for ten seconds, then output the interferential waveform 400 for thirty seconds. This may be advantageous because sending the muscle stimulation waveform 500 for ten seconds may be intense for the patient. Thus, sending the interferential waveform 400 for an extended period of time may help the patient recover faster than only resting.

The interferential waveform 400 sent during intersperse mode 700 may have an amplitude equal to a fraction of the interferential waveform 400 amplitude sent during the first segment. For example, as discussed above, a patient may gradually increase the amplitude of the interferential waveform 400 during the first segment of the therapy until a threshold output is reached. The electro-medical device 10 may apply a percentage or fraction of the threshold output to the interferential waveform 400 during the second segment. The percentage may range from 50%-150% of the first interferential waveform 400's amplitude. The percentage may be 50% when the muscle stimulation duty cycle is short, because the patient may be more sensitive to the interferential waveform 400 if the muscle stimulation waveform 500 is less intense. Conversely, the percentage may be 150% if the muscle stimulation duty cycle is longer, because the patient may be less sensitive to the interferential waveform 400 if the muscle stimulation waveform 500 is more intense.

Intersperse mode 700 may last for a pre-defined duration. The duration may vary from 10 minutes to 60 minutes. This duration may be set by the patient and may be based on the amount of pain the patient is feeling on a particular day.

Figure 8:
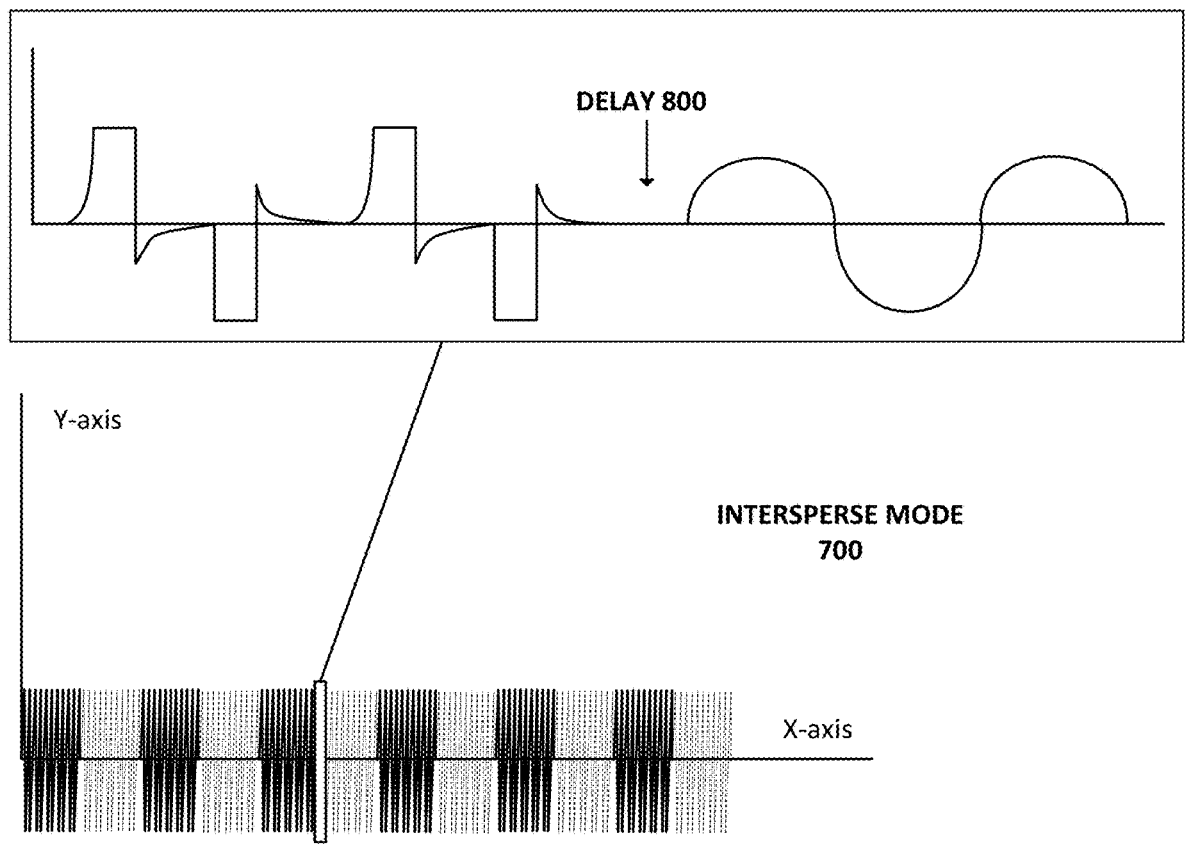
FIG. 8 shows a detailed view of the intersperse operating mode in FIG. 7, according to an example embodiment.

FIG. 8 shows a delay 800 in intersperse mode 700, according to an example embodiment. As discussed above, electro-medical device 10 alternates between sending muscle stimulation waveform 500 and interferential waveform 400 during intersperse mode 700. Additionally, there may be a delay 800 when the electro-medical device switches between the muscle stimulation waveform 500 and interferential stimulation waveform 400. The delay 800 may vary in duration from about 500 µSec to about 200 mSec (e.g., within possible tolerances of 100 µSec). The electro-medical device 10 may cause the delay 800 in order to balance out the ions when changing the output from the interferential stimulation waveform 400 to the muscle stimulation waveform 500.

Below is an example table illustrating some example operating parameters for the intersperse pain treatment.

| First segment duration (IF) | Percent of IF segment output during IS segment | Second segment duration (IS) | Delay between MS & IF in IS segment | MS "on" time in IS segment | IF "on" time in IS segment |
|---|---|---|---|---|---|
| 3 Min. | 110% | 15 Min. | 600 µSec | 5 Sec | 5 Sec |
| 5 Min. | 100% | 30 Min. | 50 mSec | 10 Sec | 10 Sec |
| 10 Min. | 80% | 30 Min. | 100 mSec | 10 Sec | 30 Sec |
| 15 Min. | 70% | 30 Min. | 200 mSec | 10 Sec | 30 Sec |

In the table above, the delay between MS and IF in the IS segment is shown with some example delay times. However, in other examples, the delay between MS and IF in the IS segment can be as low as zero seconds (or no delay).

Figure 9:
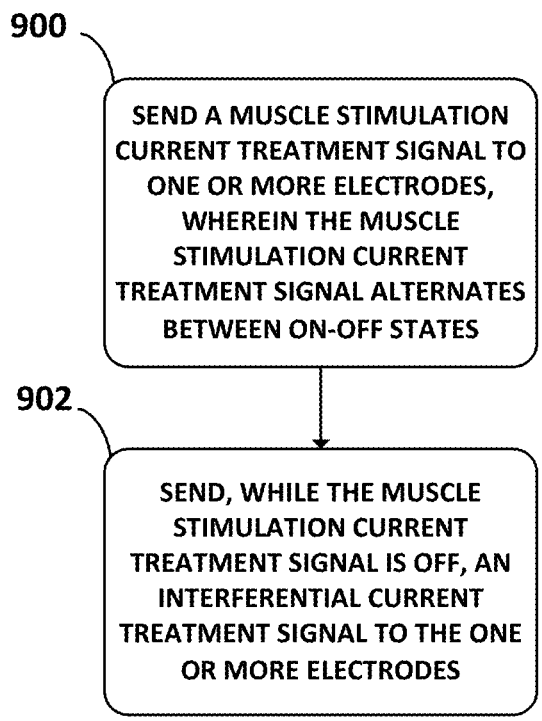
FIG. 9 is a flow chart of an example method for combination pain treatment, according to an example embodiment.

FIG. 9 is a flow chart illustrating an example embodiment. The process illustrated by FIG. 9 may be carried out by electro-medical device 10. However, the process can be carried out by other types of devices or device subsystems. For example, the process could be carried out by a portable computer, such as a laptop or a tablet device.

In addition, for the method shown in FIG. 9 and other processes and methods disclosed herein, the flowchart shows functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include a non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, a tangible storage device, or other article of manufacture, for example.

In addition, for the method and other processes and methods disclosed herein, each block in FIG. 9 may represent circuitry that is wired to perform the specific logical functions in the process.

Illustrative methods, such as method in FIG. 9, may be carried out in whole or in part by a component or components in a computing device, or the electro-medical device 10 shown in FIG. 1, or by the one or more of the components of the electro-medical device 10 shown in FIG. 1. However, it should be understood that example methods may be carried out by other entities or combinations of entities (i.e., by other computing devices and/or combinations of computing devices).

Block 900 may involve sending a muscle stimulation current treatment signal to one or more electrodes, and the muscle stimulation current treatment signal alternates between on-off states.

Block 902 may involve sending, while the muscle stimulation current treatment signal is off, an interferential current treatment signal to the one or more electrodes.

Some examples further involve receiving an input based on a calculated threshold output, and then determining an amplitude for the interferential current treatment signal based on the calculated threshold output.

Some examples further involve sending the interferential current treatment signal after a delay of about 600 µSec to about 100 mSec.

Some examples further involve sending the muscle stimulation current treatment signal with an on-off state duration of about five seconds off and about five seconds on.

Some examples further involve sending an initial interferential current treatment signal to the one or more electrodes before sending the muscle stimulation current treatment signal, wherein the initial interferential current treatment signal is continuous.

Some examples further involve sending the initial interferential current treatment signal for a duration between about three minutes and about fifteen minutes (e.g., within possible tolerances of 1 minute).

The examples of FIG. 9 may be simplified by the removal of any one or more of the features shown therein. Further, these embodiments may be combined with features, aspects, and/or implementations of any of the previous figures or otherwise described herein.

A preference trial was conducted on 13 volunteers. The subjects were asked to take a treatment with normal Sequential Stimulation one day and the next day the subjects were asked to take an Intersperse Stimulation treatment. The subjects were then requested to fill out a questionnaire that inquired about which stimulation was preferred, pain levels (pre, post, and at 1 hour and 2 hours after stimulation), level of numbness and muscle spasms. Eleven (11) of the subjects had a preexisting painful condition and two (2) of the subjects were pain free.

Sequential Stimulation consists of 15 minutes of Interferential Stimulation followed by 30 minutes of Neuromuscular Electrical Stimulation (MMES) and usually takes approximately 2-3 minutes to set the amplitude levels of the two outputs correctly. That adds up to 47-48 minutes of time to take a traditional Sequential Stimulation treatment. A duty cycle of Muscle Stimulation consists of an On time, when stimulation is occurring and it results in a muscle contraction, and an Off time, when there is no stimulation and the muscle is laying flaccid and resting. Intersperse Stimulation fills the off time of the muscle stimulation with Interferential stimulation and takes advantage of the normally down time to save approximately 15 minutes per treatment for the patient.

Eighty five percent (85%) (11/13) of the subjects preferred the Intersperse Stimulation treatment over the Sequential LAMES. A numerical rating scale of 0-10 was used for rating pain. When comparing baseline pain (pre-treatment) with post-treatment pain, the subjects that preferred Intersperse Stimulation (IS Group) reported an average pain reduction of 3.64 points and the subjects that preferred Sequential Stimulation (SS Group) reported an average pain reduction of 2.5 points which shows a 46% better pain reduction with the Intersperse Stimulation Group as compared to the Sequential Stimulation Group. When comparing only subjects that had preexisting painful conditions, the Intersperse Stimulation Group reported an average pain reduction of 4.44 points and the Sequential Stimulation Group reported an average pain reduction of 2.5 points which produced a 78% better pain reduction for the Intersperse Stimulation Group.

Subjects that preferred intersperse stimulation and had pre-existing painful conditions experienced greater immediate pain relief and it was sustained over a 2 hour period of time. The group that preferred Sequential Stimulation received less pain relief and it decreased over the 2 hour period.

Benefits of Intersperse Stimulation are that it saves treatment time and that a more complete analgesia can be achieved because Interferential Stimulation is sent through the electrodes during the normally quiescent "off time" of the MMES duty cycle. These benefits were proven through the study in which eighty five percent (85%) of subjects tested preferred Intersperse Stimulation (IS) when compared to Sequential Stimulation (SS). The IS Group experienced greater immediate pain relief and the relief was sustained over a longer period of time when compared to the SS Group.

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The description describes various features and functions of the disclosed systems, devices, and methods with reference to the accompanying figures. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the message flow diagrams, scenarios, and flow charts in the figures and as discussed herein, each step, block, and/or communication can represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages can be executed out of order from that shown or discussed, including substantially concurrently or in reverse order, depending on the functionality involved. Further, more or fewer blocks and/or functions can be used with any of the ladder diagrams, scenarios, and flow charts discussed herein, and these ladder diagrams, scenarios, and flow charts can be combined with one another, in part or in whole.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk, hard drive, or other storage medium.

The computer readable medium can also include non-transitory computer readable media such as computer-readable media that store data for short periods of time like register memory, processor cache, and random access memory (RAM). The computer readable media can also include non-transitory computer readable media that store program code and/or data for longer periods of time. Thus, the computer readable media may include secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

Moreover, a step or block that represents one or more information transmissions can correspond to information transmissions between software and/or hardware modules in the same physical device. However, other information transmissions can be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

While various aspects and embodiments have been disclosed herein, other aspects and embodiments will be apparent to those skilled in the art. The various aspects and embodiments disclosed herein are for purpose of illustration and are not intended to be limiting, with the true scope being indicated by the following claims.

What is claimed is:

1. A two-segment method of pain treatment comprising:
   in a first segment, sending a first interferential current treatment signal, by an electro-medical device, to multiple electrodes for a pre-defined period of time;
   in a second segment, sending, by the electro-medical device, a muscle stimulation current treatment signal to the multiple electrodes, wherein the muscle stimulation current treatment signal alternates between on-off states, and wherein during the on state the electro-medical device sends a continuous muscle stimulation signal for a first duration causing repeated contraction of a patient's muscle for a contract cycle with no relax cycle, and during the off state the electro-medical device sends a second interferential current treatment signal to the multiple electrodes for a second duration so as to alternate between the muscle stimulation signal and the second interferential current treatment signal during the second segment, wherein the second duration is longer than the first duration, and wherein the first duration is between about five seconds to about ten seconds.

2. The method of pain treatment of claim 1, further comprising:

receiving an input indicative of an output level of the electro-medical device; and determining an amplitude for the first interferential current treatment signal based on the received input.

3. The method of pain treatment of claim 1, wherein sending, by the electro-medical device while the muscle stimulation current treatment signal is in the off state, the second interferential current treatment signal to the multiple electrodes comprises sending the second interferential current treatment signal after a delay of about 600 μSec to about 200 mSec following the muscle stimulation current treatment signal entering the off state.

4. The method of pain treatment of claim 1, wherein sending, by the electro-medical device, the muscle stimulation current treatment signal to multiple electrodes comprises sending the muscle stimulation signal for the first duration of about ten seconds and sending the second interferential current treatment signal for the second duration of longer than ten seconds.

5. The method of pain treatment of claim 1, wherein the first interferential current treatment signal is continuous.

6. The method of pain treatment of claim 5, wherein sending the first interferential current treatment signal comprises sending the first interferential current treatment signal for a duration between about three seconds and about thirty seconds.

7. The method of pain treatment of claim 5, wherein the second interferential current treatment signal has a reduced amplitude as compared to the first interferential current treatment signal.

8. The method of pain treatment of claim 1, wherein sending the second interferential current treatment signal to the multiple electrodes comprises sending the second interferential current treatment signal to the multiple electrodes only during the off state of the muscle stimulation current treatment signal.

9. The method of pain treatment of claim 1, wherein sending the second interferential current treatment signal to the multiple electrodes comprises sending the second interferential current treatment signal to the multiple electrodes with no delay following the muscle stimulation current treatment signal entering the off state.

10. The method of pain treatment of claim 1, wherein sending the second interferential current treatment signal to the multiple electrodes comprises sending the second interferential current treatment signal after a delay following the muscle stimulation current treatment signal entering the off state.

11. An electro-medical device comprising:

one or more drive circuits having one or more channels, respectively, wherein the one or more drive circuits are configured to output treatment signals; and a processor coupled to the one or more drive circuits, wherein the processor is programmed to (i) send in a first segment, a first interferential current treatment signal through the one or more drive circuits to the one or more channels for a pre-defined period of time, and to (ii) send in a second segment, a muscle stimulation current treatment signal having an on-off duty cycle through the one or more drive circuits to the one or more channels, wherein during an on state of the on-off duty cycle a continuous muscle stimulation signal is sent through the one or more drive circuits to the one or more channels for a first duration causing repeated contraction of a patient's muscle for a contract cycle with no relax cycle, and during an off state of the on-off duty cycle a second interferential current treatment signal is sent through the one or more drive circuits to the one or more channels for a second duration so as to alternate between the continuous muscle stimulation signal and the second interferential current treatment signal during the second segment, wherein a duration of the second interferential current treatment signal is longer than a duration of the continuous muscle stimulation signal, and wherein the output treatment signals include the muscle stimulation current treatment signal and the first interferential current treatment signal, and wherein the first duration is between about five seconds to about ten seconds.

12. The electro-medical device of claim 11, wherein the second interferential current treatment signal has a reduced amplitude as compared to the first interferential current treatment signal.

13. The electro-medical device of claim 11, wherein the first interferential current treatment signal includes a pre-modulated interferential waveform that has a sinewave output with a frequency of about 5000 Hz, and wherein an amplitude of the sinewave output is modulated to simulate a beat frequency varying between 10-150 Hz.

14. The electro-medical device of claim 11, wherein the processor sends the second interferential current treatment signal after a delay of about 600 μSec to about 200 mSec following the muscle stimulation current treatment signal entering the off state.

15. The electro-medical device of claim 11, wherein the processor sends the second interferential current treatment signal only during the off state of the muscle stimulation current treatment signal.

16. The electro-medical device of claim 11, wherein the processor sends the second interferential current treatment signal with no delay following the muscle stimulation current treatment signal entering the off state.

17. The electro-medical device of claim 11, wherein the processor sends the second interferential current treatment signal after a delay following the muscle stimulation current treatment signal entering the off state.

18. The electro-medical device of claim 11, wherein the processor sends the muscle stimulation signal for the first duration of about ten seconds and sends the second interferential current treatment signal for the second duration of longer than ten seconds.

19. A non-transitory computer readable medium having stored therein instructions that, when executed by a processor of an electro-medical device, cause the electro-medical device to perform functions comprising:

in a first segment, sending a first interferential current treatment signal to multiple electrodes for a pre-defined period of time;

in a second segment, sending a muscle stimulation current treatment signal to the multiple electrodes, wherein the muscle stimulation current treatment signal alternates between on-off states, and wherein during the on state the electro-medical device sends a continuous muscle stimulation signal for a first duration causing repeated contraction of a patient's muscle for a contract cycle with no relax cycle, and during the off state the electro-medical device sends a second interferential current treatment signal to the multiple electrodes for a second duration so as to alternate between the muscle stimulation signal and the second interferential current treatment signal during the second segment, wherein the second duration is longer than the first duration, and wherein the first duration is between about five seconds to about ten seconds.

* * * * *